(12) United States Patent
Matsumoto

(10) Patent No.: US 10,488,640 B2
(45) Date of Patent: *Nov. 26, 2019

(54) IMAGE ACQUISITION DEVICE AND IMAGE ACQUISITION METHOD

(71) Applicant: HAMAMATSU PHOTONICS K.K., Hamamatsu-shi, Shizuoka (JP)

(72) Inventor: Naoya Matsumoto, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 108 days.

This patent is subject to a terminal disclaimer.

(21) Appl. No.: 15/544,129

(22) PCT Filed: Jan. 12, 2016

(86) PCT No.: PCT/JP2016/050700
§ 371 (c)(1),
(2) Date: Jul. 17, 2017

(87) PCT Pub. No.: WO2016/117415
PCT Pub. Date: Jul. 28, 2016

(65) Prior Publication Data
US 2018/0267283 A1    Sep. 20, 2018

(30) Foreign Application Priority Data

Jan. 20, 2015    (JP) ................... 2015-008445

(51) Int. Cl.
*G02B 21/00* (2006.01)
*H04N 13/254* (2018.01)
(Continued)

(52) U.S. Cl.
CPC ......... *G02B 21/0032* (2013.01); *G01N 21/64* (2013.01); *G02B 21/008* (2013.01);
(Continued)

(58) Field of Classification Search
CPC .. G02B 21/0032; G02B 21/367; G02B 21/26; G02B 21/008; G02B 21/08;
(Continued)

(56) References Cited

U.S. PATENT DOCUMENTS 5,982,553 A * 11/1999 Bloom ................. G02B 5/1828
                                                                    359/627
6,028,306 A *  2/2000 Hayashi ............ G02B 21/0032
                                                                    250/235
(Continued)

FOREIGN PATENT DOCUMENTS

CN    100559165 C    11/2009
CN    102162908 A     8/2011
(Continued)

OTHER PUBLICATIONS

Wan Qin et al., "Addressable discrete-line-scanning multiphoton microscopy based on a spatial light modulator," Optics Letters, Mar. 1, 2012, pp. 827-829, vol. 37, No. 5.

(Continued)

*Primary Examiner* — Gims S Philippe
*Assistant Examiner* — Stefan Gadomski
(74) *Attorney, Agent, or Firm* — Drinker Biddle & Reath LLP

(57) ABSTRACT

An image acquisition device includes a spatial light modulator modulating irradiation light, a control unit controlling a modulating pattern so that a plurality of light converging points are formed in an observation object, a light converging optical system converging the modulated irradiation light, a scanning unit scanning positions of the plurality of light converging points in the observation object in a scanning direction intersecting an optical axis of the light converging optical system, and a photodetector configured to detect a plurality of observation lights generated from the (Continued)

US 10,488,640 B2

Page 2 plurality of light converging points. The control unit sets a center spacing between adjacent light converging points on the basis of the positions of the plurality of light converging points in a direction of the optical axis.

26 Claims, 13 Drawing Sheets

(51) Int. Cl.
*H04N 13/125* (2018.01)
*H04N 13/218* (2018.01)
*G02B 21/36* (2006.01)
*G02B 21/08* (2006.01)
*G02B 21/26* (2006.01)
*G01N 21/64* (2006.01)
*G02B 21/06* (2006.01)
*G02B 26/10* (2006.01)
*G02F 1/01* (2006.01)
*G02B 26/08* (2006.01)
*G02B 27/00* (2006.01)

(52) U.S. Cl.
CPC ..... *G02B 21/0036* (2013.01); *G02B 21/0076* (2013.01); *G02B 21/06* (2013.01); *G02B 21/08* (2013.01); *G02B 21/26* (2013.01); *G02B 21/36* (2013.01); *G02B 21/367* (2013.01); *G02B 26/10* (2013.01); *G02F 1/01* (2013.01); *H04N 13/125* (2018.05); *H04N 13/218* (2018.05); *H04N 13/254* (2018.05); *G02B 26/0808* (2013.01); *G02B 26/0833* (2013.01); *G02B 27/0031* (2013.01)

(58) Field of Classification Search
CPC ............ G02B 21/0036; G02B 21/0076; G02B 26/10; G02B 21/36; G02B 21/06; G02B 26/0808; G02B 27/0031; G02B 26/0833; H04N 13/125; H04N 13/254; H04N 13/218; G01N 21/64; G02F 1/01
See application file for complete search history.

(56) References Cited

U.S. PATENT DOCUMENTS

| | | | | |
|---|---|---|---|---|
| 6,758,402 | B1* | 7/2004 | Check | G02B 26/10 235/462.25 |
| 7,098,871 | B1* | 8/2006 | Tegreene | G02B 26/101 345/7 |
| 7,709,773 | B2* | 5/2010 | Yamashita | G01N 21/6456 250/201.3 |
| 8,526,091 | B2* | 9/2013 | Ito | B23K 26/032 359/238 |
| 9,188,874 | B1* | 11/2015 | Johnson | G03F 7/70291 |
| 2003/0021016 | A1* | 1/2003 | Grier | G02B 21/0036 359/368 |
| 2007/0057211 | A1* | 3/2007 | Bahlman | G01N 21/6452 250/584 |
| 2007/0262264 | A1* | 11/2007 | Hasegawa | G01N 21/6408 250/458.1 |
| 2008/0297730 | A1 | 12/2008 | Park et al. | |
| 2009/0147330 | A1* | 6/2009 | Seo | B23K 26/38 359/11 |
| 2010/0014088 | A1* | 1/2010 | Wiki | G01N 21/253 356/445 |
| 2011/0134516 | A1 | 6/2011 | Araya et al. | |
| 2011/0137126 | A1* | 6/2011 | French | A61B 1/00165 600/178 |
| 2011/0267663 | A1* | 11/2011 | Murayama | G03H 1/08 359/9 |
| 2011/0273757 | A1* | 11/2011 | Kobayashi | A61B 3/102 359/204.2 |
| 2012/0327501 | A1* | 12/2012 | Sakamoto | B23K 26/40 359/290 |
| 2012/0329247 | A1* | 12/2012 | Sakamoto | B23K 26/40 438/462 |
| 2014/0146159 | A1* | 5/2014 | Liu | G02B 21/006 348/79 |
| 2015/0323787 | A1* | 11/2015 | Yuste | G02B 27/0075 348/79 |
| 2016/0018786 | A1* | 1/2016 | Matsumoto | G01N 21/6458 359/9 |
| 2016/0178880 | A1* | 6/2016 | Yamazaki | G02B 21/0048 359/201.2 |
| 2017/0205613 | A1* | 7/2017 | Fukuyama | G02B 21/0092 |

FOREIGN PATENT DOCUMENTS

| | | |
|---|---|---|
| CN | 103226238 A | 7/2013 |
| CN | 103403610 A | 11/2013 |
| EP | 1889111 A2 | 2/2008 |
| EP | 2703871 A2 | 3/2014 |
| JP | H06-094641 A | 4/1994 |
| JP | H10-311950 A | 11/1998 |
| JP | 2004-138906 A | 5/2004 |
| JP | 2006-071611 A | 3/2006 |
| JP | 2009-175441 A | 8/2009 |
| JP | 2011-128572 A | 6/2011 |
| JP | 2011-527218 A | 10/2011 |
| JP | 2012-226268 A | 11/2012 |
| JP | 2013-225118 A | 10/2013 |
| JP | 2014-006308 A | 1/2014 |
| WO | WO 2006/127967 A2 | 11/2006 |
| WO | WO 2010/004297 A1 | 1/2010 |
| WO | WO 2014/117079 A1 | 7/2014 |
| WO | WO-2014/136784 A1 | 9/2014 |

OTHER PUBLICATIONS

Yonghong Shao et al., "Addressable multiregional and multifocal multiphoton microscopy based on a spatial light modulator", Journal of Biomedical Optics, Apr. 3, 2012, p. 030505-1-p. 030505-3, XP055495857.
Junle Qu et al., "Recent Progress in Multifocal Multiphoton Microscopy", Journal of Innovative Optical Health Sciences: JIOHS, vol. 05, No. 03, Aug. 4, 2012, p. 1250018, XP055494346.
P.A. Young et al., "The effects of spherical aberration on multiphoton fluorescence excitation microscopy: Effects of Spherical Aberration on MPM", Journal of Microscopy, Oct. 11, 2010, p. 157-p. 165, XP055495938.
Jorg Bewersdorf et al., "Multifocal Multi-Photon Microscopy In: Handbook of Biological Confocal Microscopy", Springer Science + Business Media, Jan. 31, 2006, p. 550-p. 560, XP055039836.
International Preliminary Report on Patentability dated Aug. 3, 2017 for PCT/JP2016/050700.
English-language translation of International Preliminary Report on Patentability (IPRP) dated Apr. 19, 2016 that issued in WO Patent Application No. PCT/JP2016/050665.
Li, Ge, et al., "Enumeration of illumination and scanning modes from real-time spatial light modulators", Optics Express, vol. 7, No. 12, Dec. 4, 2000, p. 403, XP055496180.
Volodymyr, Nikolenko, et al., "SLM microscopy scanless two-photon imaging and photostimulation using spatial light modulators", Frontiers in Neural Circuits, vol. 2, Jan. 31, 2008, XP055146495.

* cited by examiner (a)

(b)

(a)

(b)

IMAGE ACQUISITION DEVICE AND IMAGE ACQUISITION METHOD

TECHNICAL FIELD

An aspect of the present invention relates to an image acquisition device and an image acquisition method.

BACKGROUND ART

Non-Patent Literature 1 discloses a multiphoton absorption microscope using a spatial light modulator (SLM). This microscope is intended to acquire a fluorescence image from within an observation object at high speed and clearly by forming and scanning a plurality of excitation light spots using the SLM.

CITATION LIST

Patent Literature

[Patent Literature 1] Japanese Unexamined Patent Publication No. 2012-226268

Non Patent Literature

[Non-Patent Literature 1] Wan Qin, Yonghong Shao, Honghai Liu, Xiang Peng, Hanben Niu, and Bruce Gao, "Addressable discrete-line-scanning multiphoton microscopy based on spatial light modulator", OPTICS LETTERS, Vol. 37, No. 5, pp. 827-829, Mar. 1, 2012

Because a plurality of portions can be simultaneously observed by simultaneously radiating light to a plurality of positions of an observation object in microscopic observation, there an advantage in that it is possible to shorten an observation time and acquire states of a plurality of portions at the same time. Because of this, it is necessary to simultaneously radiate light to a plurality of positions and simultaneously detect the observation light generated from these positions using a photodetector having, for example, a plurality of detection areas. However, when the observation light is detected in this manner, the following problems may occur.

When the irradiation light is radiated to the observation object, aberration (for example, spherical aberration) caused by the surface shape of the observation object occurs. In order to correct such aberration, it is preferable to control the wavefront of the irradiation light using, for example, an SLM. However, it is difficult to perform such correction for the observation light generated from the observation object in many cases. Accordingly, the mode of the observation light reaching the photodetector is affected by the aberration. That is, observation light generated at a deep position in the observation object has a larger light diameter at the time of arrival at the objective lens than observation light generated at a shallow position in the observation object. Accordingly, likewise, also in the photodetector, the light diameter of the observation light generated at a deep position is larger than the light diameter of the observation light generated at a shallow position.

In microscopic observation, when a thick observation object is observed from a shallow position to a deep position, the light diameter of the observation light differs according to an observation depth due to the above-described phenomenon. Accordingly, when a plurality of observation lights generated from a plurality of positions are simultaneously detected, adjacent observation lights overlap each other in the photodetector according to the observation depth and crosstalk may occur. When crosstalk occurs, it becomes difficult to accurately detect each of the plurality of observation lights.

An aspect of the present invention is to provide an image acquisition device and an image acquisition method capable of reducing crosstalk due to overlapping of a plurality of observation lights.

Solution to Problem

An image acquisition device according to an embodiment of the present invention is a device for acquiring an image of an observation object including: a spatial light modulator modulating irradiation light output from a light source; a control unit controlling a modulating pattern to be presented on the spatial light modulator so that a plurality of light converging points are formed in an observation object; a light converging optical system converging the modulated irradiation light so that the plurality of light converging points are formed in the observation object; a scanning unit scanning positions of the plurality of light converging points in the observation object in a scanning direction intersecting an optical axis of the light converging optical system; a photodetector detecting a plurality of observation lights generated from the plurality of light converging points; and an image creating unit creating an image of the observation object using a detection signal from the photodetector. The control unit sets a center spacing between adjacent light converging points on the basis of the positions of the plurality of light converging points in a direction of the optical axis.

Also, an image acquisition device according to another embodiment of the present invention is a device for acquiring an image of an observation object including: a spatial light modulator modulating irradiation light output from a light source; a control unit controlling a modulating pattern to be presented on the spatial light modulator so that a plurality of light converging points are formed in an observation object; a light converging optical system converging the modulated irradiation light so that the plurality of light converging points are formed in the observation object; a photodetector detecting a plurality of observation lights generated from the plurality of light converging points; and an image creating unit creating an image of the observation object using a detection signal from the photodetector. The modulating pattern includes a pattern for scanning the plurality of light converging points in a scanning direction intersecting an optical axis of the irradiation light. The control unit sets a center spacing between adjacent light converging points on the basis of positions of the plurality of light converging points in a direction of the optical axis.

Also, an image acquisition method according to an embodiment of the present invention is a method of acquiring an image of an observation object, the method including the steps of: presenting a modulating pattern for forming a plurality of light converging points in an observation object on a spatial light modulator; modulating irradiation light output from a light source in the spatial light modulator and converging the modulated irradiation light by a light converging optical system so that the plurality of light converging points are formed in the observation object; detecting a plurality of observation lights generated from the plurality of light converging points while scanning positions of the plurality of light converging points in the observation object in a scanning direction intersecting an optical axis of the irradiation light; and creating an image of the observation object using a detection signal obtained in the light detecting step. A center spacing between adjacent light converging points is set on the basis of the positions of the plurality of light converging points in a direction of the optical axis in the pattern presenting step.

In the image acquisition device and the image acquisition method, it is possible to simultaneously and easily form a plurality of light converging points by presenting a modulating pattern on the spatial light modulator. Then, the plurality of light converging points are scanned and the plurality of observation lights generated from the plurality of light converging points are detected. In this manner, according to the image acquisition device and the image acquisition method described above, it is possible to simultaneously radiate a plurality of lights to the observation object and further simultaneously detect a plurality of observation lights. Accordingly, it is possible to shorten an observation time and easily acquire states of a plurality of portions at the same time.

Also, when the plurality of observation lights generated from the plurality of positions are simultaneously detected as described above, adjacent observation lights overlap each other in the photodetector according to the observation depth and crosstalk may occur. On the other hand, in the image acquisition device and the image acquisition method described above, a center spacing between adjacent light converging points is set on the basis of the positions of the plurality of light converging points in the direction of the optical axis (that is, the observation depth). Thereby, for example, because it is possible to widen the center spacing between adjacent light converging points when the light diameter of the observation light increases in the photodetector, it is possible to prevent a plurality of observation lights from overlapping one another and reduce crosstalk. Accordingly, it is possible to accurately detect each of the plurality of observation lights and provide a clear image of the observation object.

Also, in the above-described image acquisition device, the control unit may change the center spacing according to a change in the positions of the plurality of light converging points in the direction of the optical axis. Likewise, the center spacing may be changed according to a change in the positions of the plurality of light converging points in the direction of the optical axis in the pattern presenting step of the image acquisition method. Thereby, it is possible to continuously perform observation of a plurality of depths while suppressing crosstalk. In this case, the control unit increases the center spacing as the positions of the plurality of light converging points in the direction of the optical axis are distanced further from a surface of the observation object (or in the pattern presenting step). Thereby, it is possible to suitably reduce crosstalk of the observation light due to aberration of a surface of the observation object.

Also, in the above-described image acquisition device, the scanning unit may include a light scanner receiving the modulated irradiation light or include a stage moving the observation object in the scanning direction while holding the observation object. Also, in the light detecting step of the above-described image acquisition method, scanning of the plurality of light converging points may be performed using a light scanner receiving the modulated irradiation light, scanning of the plurality of light converging points may be performed using a stage moving the observation object in the scanning direction while holding the observation object, or a pattern for scanning the plurality of light converging points may be superimposed on the modulating pattern. According to any one thereof, it is possible to suitably scan positions of the plurality of light converging points.

Also, in the above-described image acquisition device, the photodetector may have a plurality of detection areas for detecting the plurality of observation lights and sizes of the plurality of detection areas and a center spacing between the detection areas may be set on the basis of the positions of the plurality of light converging points in the direction of the optical axis. Likewise, in the light detecting step of the above-described image acquisition method, a photodetector having a plurality of detection areas for detecting the plurality of observation lights may be used and the plurality of detection areas may be set on the basis of the positions of the plurality of light converging points in the direction of the optical axis. Thereby, because a pitch between and sizes of the plurality of detection areas are set according to a center spacing between observation lights and/or the light diameter, it is possible to suitably detect a plurality of observation lights.

Also, in the above-described image acquisition device, the photodetector may output a plurality of image data corresponding to the plurality of detection areas as the detection signal and the image creating unit may combine the plurality of image data to create the image of the observation object. Likewise, in the above-described image acquisition method, the photodetector may output a plurality of image data corresponding to the plurality of detection areas as the detection signal, and the plurality of image data may be combined to create an image of the observation object in the image creating step. Thereby, because it is possible to divide an area to be observed in the observation object into a plurality of areas and create images of the areas in parallel, an observation time can be effectively shortened.

Also, in the above-described image acquisition device, the photodetector may include a multi-anode photomultiplier tube having a plurality of anodes or include an area image sensor having a plurality of pixels. Likewise, in the light detecting step of the above-described image acquisition method, the plurality of the observation lights may be detected using a multi-anode photomultiplier tube having a plurality of anodes and the plurality of the observation lights may be detected using an area image sensor having a plurality of pixels. According to any one thereof, it is possible to accurately detect a plurality of observation lights.

Also, in the above-described image acquisition device and image acquisition method, the plurality of light converging points may be arranged in a direction intersecting the scanning direction when viewed from the direction of the optical axis. Thereby, because it is possible to divide an area to be observed in the observation object into a plurality of areas and create images of the areas in parallel, an observation time can be effectively shortened.

Also, the control unit may further set the center spacing between adjacent light converging points on the basis of an amount of aberration of a plurality of light converging points in a direction of an optical axis. Likewise, in the pattern presenting step of the above-described image acquisition method, the center spacing between adjacent light converging points may be further set on the basis of amounts of aberration of a plurality of light converging points in a direction of the optical axis. Thereby, it is possible to suitably reduce the crosstalk of the observation light due to aberration in the observation object.

Advantageous Effects of Invention

According to an image acquisition device and an image acquisition method according to aspects of the present invention, it is possible to simultaneously radiate a plurality of lights for which light converging positions are different in a depth direction of an observation object.

DESCRIPTION OF EMBODIMENTS

Hereinafter, embodiments of an image acquisition device and an image acquisition method according to aspects of the present invention will be described in detail with reference to the accompanying drawings. The same elements are denoted by the same reference signs in the description of the drawings, and redundant description thereof will be omitted.

Figure 1:
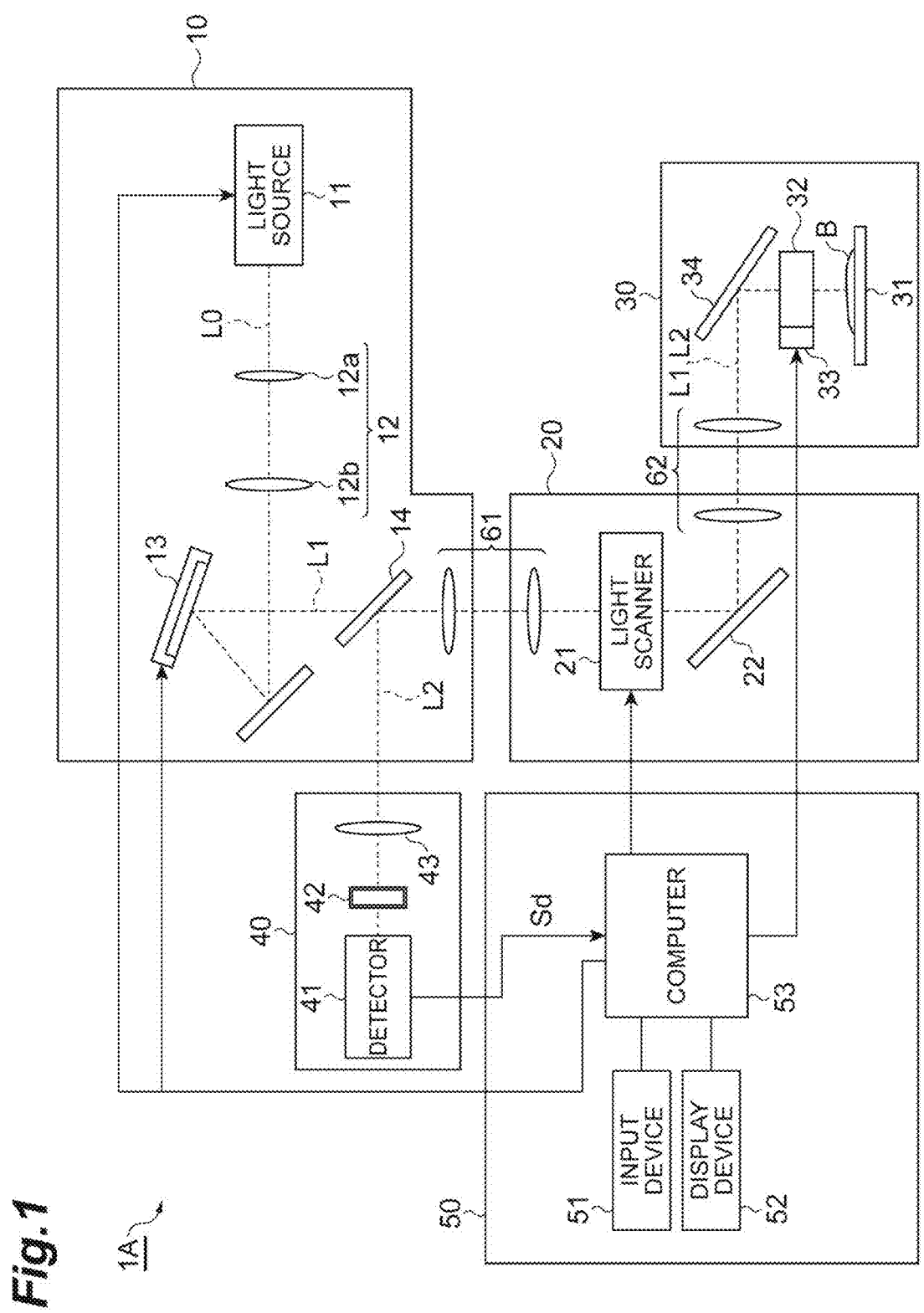
FIG. 1 is a diagram illustrating a configuration of an image acquisition device according to an embodiment of the present invention.

FIG. 1 is a diagram illustrating a configuration of an image acquisition device 1A according to an embodiment of the present invention. The image acquisition device 1A is a device for radiating irradiation light L1 to an observation object B and observing observation light (detected light) L2 generated in the observation object B by the irradiation light L1. The image acquisition device 1A is, for example, a microscope device. As the microscope device, for example, an upright microscope or an inverted microscope can be included. The observation light L2 is, for example, fluorescence, phosphorescence, high-frequency generated light (SHG), reflected light, transmitted light, scattered light, or the like. As illustrated in FIG. 1, the image acquisition device 1A includes an irradiation light generating unit 10, a scanning unit 20, a irradiation optical unit 30, an observation unit 40, and a control unit 50.

The irradiation light generating unit 10 generates the irradiation light L1 to be radiated to the observation object B. The irradiation light generating unit 10 of the present embodiment includes a light source 11, a beam expander 12, and a spatial light modulator (SLM) 13.

The light source 11 outputs irradiation light L0. The irradiation light L0 includes, for example, light having a wavelength to be radiated to the observation object B. The light source 11 is configured to include, for example, a laser light source which oscillates pulsed light or continuous wave, an SLD light source, an LED light source, or the like. The beam expander 12 includes, for example, a plurality of lenses 12a and 12b arranged side by side on the optical axis of the irradiation light L0, and adjusts the size of a cross section perpendicular to the optical axis of the irradiation light L0. Also, the lenses 12a and 12b may be convex lenses, concave lenses, or combinations thereof.

The spatial light modulator 13 is optically coupled to the light source 11 and modulates the irradiation light L0 from the light source 11, thereby generating the irradiation light L1 to be radiated to the observation object B. The spatial light modulator 13 has a plurality of pixels arranged two-dimensionally, and modulates an intensity or phase of the irradiation light L0 output from the light source 11 for each of a plurality of pixel columns. The modulating pattern (hologram) to be presented on the spatial light modulator 13 is controlled by the control unit 50 to be described below. The spatial light modulator 13 may be of a phase modulation type or an amplitude (intensity) modulation type. Also, the spatial light modulator 13 may be either a reflection type or a transmission type. Also, a plurality of spatial light modulators 13 may be provided. In this case, the irradiation light L0 is modulated a plurality of times.

The scanning unit 20 is an example of a scanning unit in the present embodiment. The scanning unit 20 has a light scanner 21 as a scanning optical system. The light scanner 21 is optically coupled to the spatial light modulator 13, and receives the irradiation light L1 modulated by the spatial light modulator 13. Also, the light scanner 21 scans an irradiation position of the irradiation light L1 on the observation object B. Further, the light scanner 21 receives the observation light L2 generated at the light converging point of the observation object B. Thereby, the observation light L2 is de-scanned. The light scanner 21 is controlled by the control unit 50 to be described below. The light scanner 21 includes, for example, a galvanometer mirror, a resonance mirror, an MEMS mirror, a two-dimensional acousto-optic element (AOM), a polygon mirror, or the like. When the light scanner 21 is a biaxial scanner, the light scanner 21 may include an image transferring optical system such as a telecentric optical system.

In addition to the light scanner 21, the scanning unit 20 may further include a mirror 22. The mirror 22 bends an optical axis of the irradiation light L1 to optically couple the light scanner 21 and the irradiation optical unit 30.

The irradiation optical unit 30 irradiates the observation object B with the irradiation light L1 provided from the scanning unit 20 and outputs the observation light L2 from the observation object B to the observation unit 40. The irradiation optical unit 30 includes a stage 31, an objective lens 32, an objective lens moving mechanism 33, and a reflection mirror 34. A dichroic mirror may be used as the reflection mirror 34.

The stage 31 is a member for supporting the observation object B (or a container such as a glass slide, a Petri dish, a microplate, a glass bottomed dish, or the like that contains the observation object B). The stage 31 is made of, for example, glass. In the example illustrated in FIG. 1, the irradiation light L1 is radiated from a front side of the stage 31, but the irradiation light L1 may be radiated from a back side of the stage 31 to the observation object B through the stage 31. The stage 31 can move in a plane direction intersecting (for example, orthogonal to) the optical axis of the objective lens 32 to be described below, while holding the observation object B. Also, the stage 31 may be movable in the optical axis direction of the objective lens 32.

The objective lens 32 is arranged to face the observation object B and is a light converging optical system that forms a light converging point of the irradiation light L1 inside the observation object B. Also, the objective lens 32 receives the observation light L2 generated at the light converging point of the observation object B and collimates the observation light L2. An objective lens for the irradiation light L1 and an objective lens for the observation light L2 may be provided separately. For example, an objective lens having a high numerical aperture (NA) may be used for the irradiation light L1, and the objective lens may locally converge light through aberration correction by the spatial light modulator 13. Also, more light can be extracted using an objective lens with a large pupil for the observation light L2. The objective lens for the irradiation light L1 and the objective lens for the observation light L2 are arranged to sandwich the observation object B and the transmitted light on the observation object B of the irradiation light L1 may be acquired as the observation light L2.

The objective lens moving mechanism 33 is a mechanism for moving the objective lens 32 in the optical axis direction of the irradiation light L1. The objective lens moving mechanism 33 includes, for example, a stepping motor or a piezoelectric actuator.

The reflection mirror 34 reflects the irradiation light L1 reaching the irradiation optical unit 30 from the irradiation light generating unit 10 toward the objective lens 32. Also, the reflection mirror 34 reflects the observation light L2 from the observation object B toward the scanning unit 20.

When a distance between the objective lens 32 and the spatial light modulator 13 is long, at least one telocentric optical system may be provided on the optical axis of the irradiation light L1 and the observation light L2. As an example, FIG. 1 illustrates two telecentric optical systems 61 and 62. The telecentric optical systems 61 and 62 serve to transfer the wavefront of the irradiation light L1 generated in the spatial light modulator 13 to a rear focal point of the objective lens 32. The telecentric optical systems 61 and 62 may be double-sided telecentric optical systems. In this case, the telecentric optical system 61 arranged between the spatial light modulator 13 and the light scanner 21 is adjusted to form an image on a modulation surface of the spatial light modulator 13 and a scanning surface of the light scanner 21. The telecentric optical system 62 arranged between the light scanner 21 and the objective lens 32 is adjusted to form an image on the scanning surface of the light scanner 21 and the pupil surface of the objective lens 32. Also, if the wavefront of the irradiation light L1 generated by the spatial light modulator 13 can be transferred to the rear focal point of the objective lens 32, the telecentric optical systems 61 and 62 may be an image-side telecentric optical system or an object-side telecentric optical system. Also, when the distance between the objective lens 32 and the spatial light modulator 13 is extremely small, it is also possible to omit the telecentric optical system.

The observation unit 40 has a photodetector 41, a filter 42, and a converging lens 43. The photodetector 41 is optically coupled to the objective lens 32 and the light scanner 21 and receives the observation light L2 to detect a light intensity of the observation light L2. The photodetector 41 is optically coupled to the light scanner 21 via a dichroic mirror 14 provided in the irradiation light generating unit 10. The dichroic mirror 14 is arranged at a position at which the irradiation light L1 modulated by the spatial light modulator 13 and the observation light L2 de-scanned by the light scanner 21 are received, transmits at least a part of the irradiation light L1, and reflects at least a part of the observation light L2. The photodetector 41 detects the light intensity of the observation light L2 and outputs a detection signal Sd. The photodetector 41 may include a multi-anode type photomultiplier tube (PMT) having a plurality of anodes, a photodiode array in which a plurality of photodiodes are configured to be arranged in an array shape, or an avalanche photodiode array in which a plurality of avalanche photodiodes are arranged in an array shape. Alternatively, the photodetector 41 may be an area image sensor having a plurality of pixels such as a CCD image sensor, an EM-CCD image sensor, or a CMOS image sensor or may be a line sensor. In particular, the multi-anode type PMT has a high multiplication factor and has a larger light receiving surface than the others.

The filter 42 is arranged on the optical axis between the dichroic mirror 14 and the photodetector 41. The filter 42 cuts out wavelengths of the irradiation light L1 and wavelengths of fluorescence or the like unnecessary for observation from light incident on the photodetector 41. The converging lens 43 is arranged immediately in front of the photodetector 41 and converges the observation light L2 toward the photodetector 41. Also, the filter 42 may be arranged at either the front stage or the rear stage of the converging lens 43. Also, when the filter 42 is unnecessary, it is unnecessary to provide the filter 42.

The control unit 50 controls the irradiation light generating unit 10, the scanning unit 20, and the irradiation optical unit 30. For example, the control unit 50 controls the light source 11, the spatial light modulator 13, and the light scanner 21. Also, for example, the control unit 50 controls the position (height) of the objective lens 32 in the optical axis direction using the objective lens moving mechanism 33. Also, for example, the control unit 50 moves the stage 31 which supports the observation object B in a direction intersecting the optical axis direction. The control unit 50 is configured to include an input device 51 such as a mouse and a keyboard, a display device 52 such as a display, and a computer 53.

Also, the computer 53 is an example of an image creating unit according to this embodiment. The computer 53 is a personal computer, a smart device or the like and includes an image processing circuit (image processing processor), a control circuit (control processor), and an internal memory. The computer 53 creates an image of the observation object B using the detection signal Sd from the photodetector 41 and light irradiation position information in the light scanner 21. The created image is displayed on the display device 52. Also, the computer 53 is an example of a control unit (controller) in the present embodiment. The computer 53 controls a modulating pattern (hologram) to be presented on the spatial light modulator 13 so that a desired light converging point is formed in the observation object B. The computer 53 controls a modulation amount of intensity or phase for each of a plurality of pixels of the spatial light modulator 13 by controlling the modulating pattern to be presented on the spatial light modulator 13. The created image may be stored in the memory of the computer 53 or the external storage device.

Figure 2:
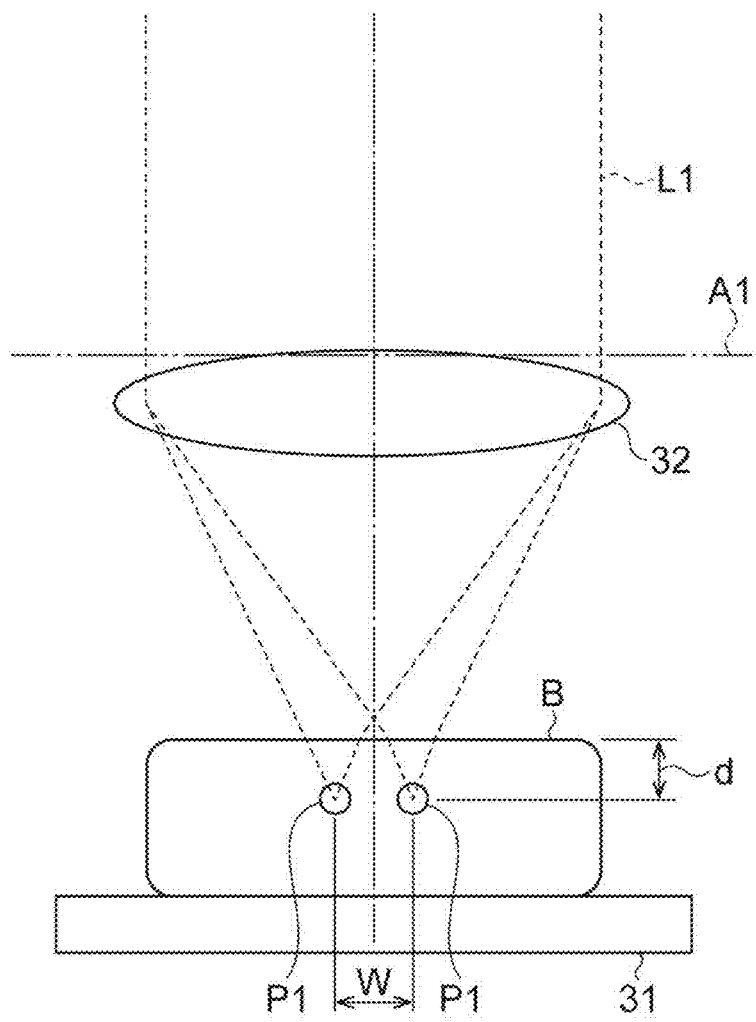
FIG. 2 is a diagram conceptually illustrating states of irradiation light on an observation object and its vicinity.
Figure 3:
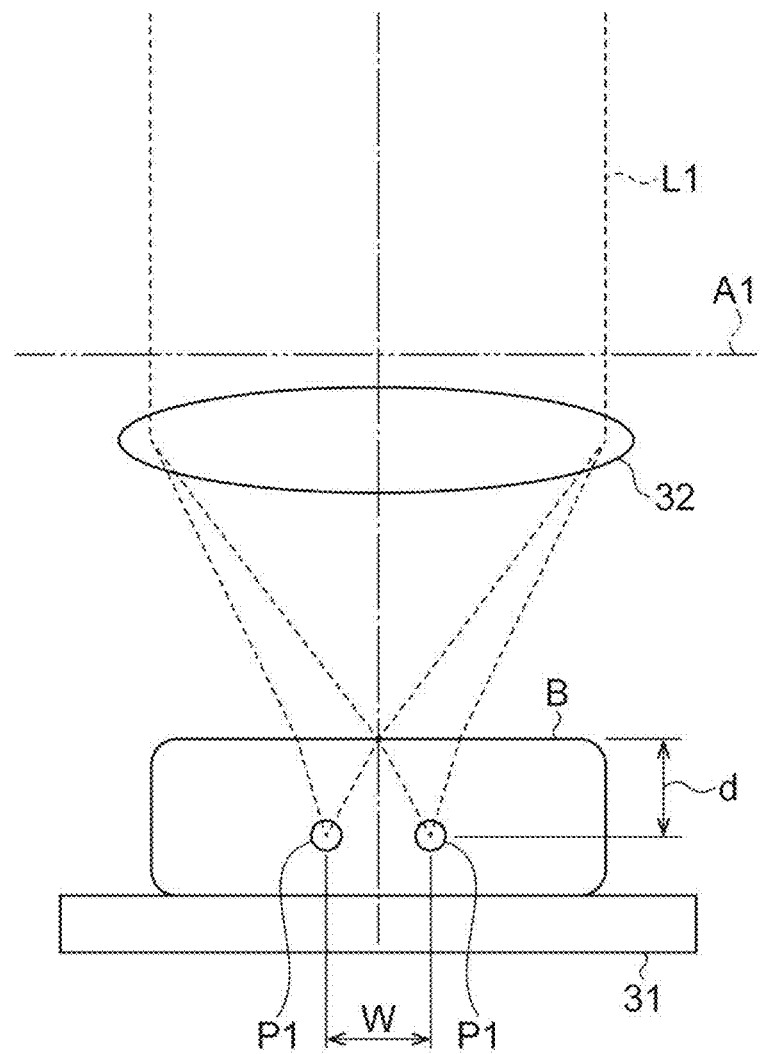
FIG. 3 is a diagram conceptually illustrating states of irradiation light on an observation object and its vicinity.

Here, the aspect of the light converging point of the observation object B will be described in detail. FIGS. 2 and 3 are diagrams conceptually illustrating states of irradiation light L1 in the observation object B and its vicinity. As illustrated in FIGS. 2 and 3, in the present embodiment, the irradiation light L1 is converged on a plurality of light converging points P1 by the objective lens 32. When the number of light converging points is three or more, FIGS. 2 and 3 illustrate two adjacent light converging points P1 of the plurality of light converging points P1 in an enlarged manner. A virtual line A1 in FIGS. 2 and 3 is a reference line representing a reference height of the objective lens 32.

The position of the light converging points P1 in the optical axis direction of the objective lens 32 (in other words, the depth direction of the observation object B) is different between FIGS. 2 and 3. That is, a case in which the depth d of the light converging points P1 from the surface of the observation object B is shallow is illustrated in FIG. 2 and a case in which the depth d of the light converging points P1 from the surface of the observation object B is deep is illustrated in FIG. 3. In other words, the light converging points P1 illustrated in FIG. 3 are further away from the surface of the observation object B than the light converging points P1 illustrated in FIG. 2.

The center spacing between the light converging points P1 in the direction orthogonal to the optical axis direction of the objective lens 32 is set on the basis of positions of the light converging points P1 in the optical axis direction of the objective lens 32. For example, as illustrated in FIG. 2, when the depth d of the light converging points P1 is shallow, the computer 53 sets the center spacing W between adjacent light converging points P1 to a narrow distance. Also, as illustrated in FIG. 3, when the depth d of the light converging points P1 is deep, the computer 53 sets the center spacing W between adjacent light converging points Pt to a wide distance. As described above, the computer 53 sets the center spacing between adjacent light converging points P1 to a wider distance as the position of the light converging points P1 in the optical axis direction of the objective lens 32 is distanced further from the surface of the observation object B. Such setting is performed through control of the modulating pattern to be presented on the spatial light modulator 13. Also, the computer 53 changes the center spacing W between adjacent light converging points P1 each time in correspondence with a change in an observation depth d, i.e., a change in the position of the light converging points P1 in the optical axis direction of the objective lens 32.

Also, the center spacing between the light converging points P1 in the direction orthogonal to the optical axis direction of the objective lens 32 is further set on the basis of amounts of aberration on the surface and/or the inside of the observation object B. For example, the center spacing between the light converging points P1 is set to be wide when the amount of aberration is large and the center spacing between the light converging points P2 is set to be narrow when the amount of aberration is small. Such setting is performed through control of the modulating pattern to be presented on the spatial light modulator 13. Also, the amounts of aberration on the surface and/or the inside of the observation object B may be actually measured or obtained or may be estimated and obtained through simulation or the like.

Figure 4:
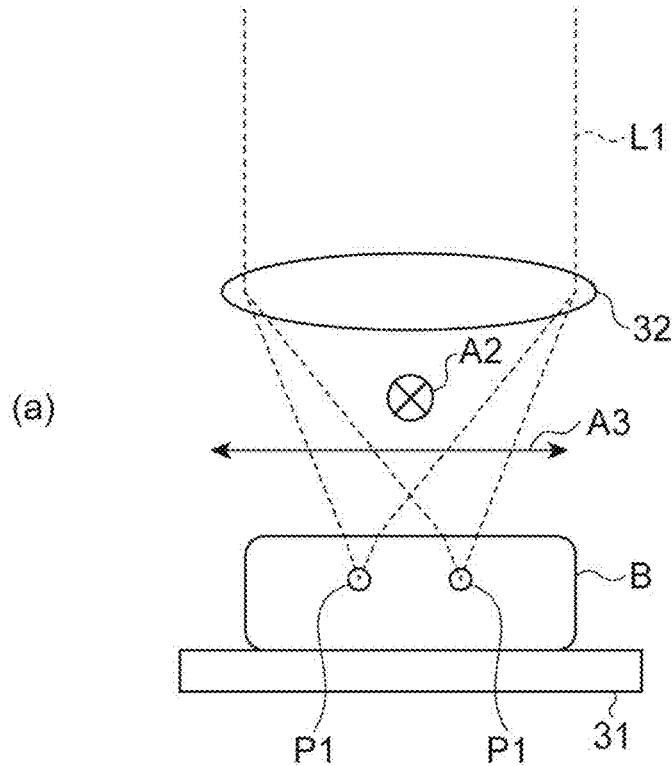
FIG. 4 is a diagram schematically illustrating an example of an arrangement direction of light converging points viewed from an optical axis direction of an objective lens.
Figure 4:
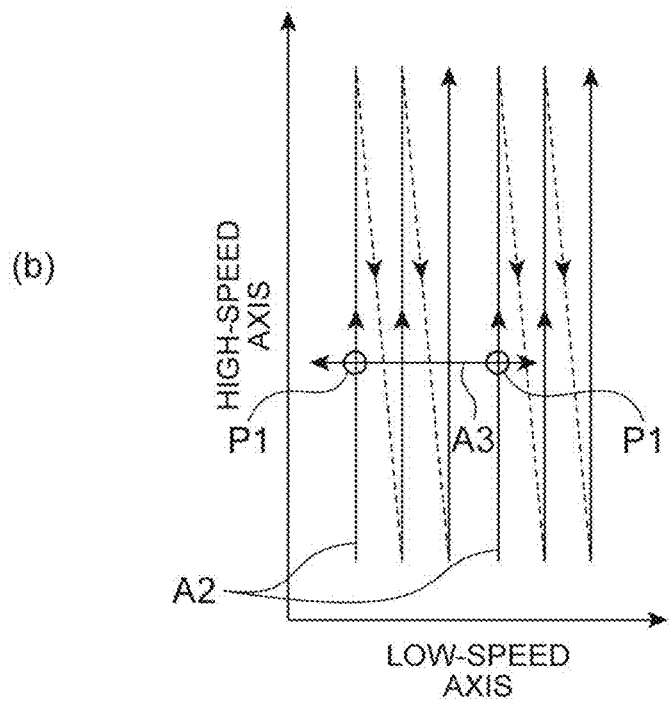

FIG. 4 is a diagram schematically illustrating an example of the arrangement direction of the light converging points P1 viewed from the optical axis direction of the objective lens 32. FIG. 4(a) illustrates a scanning direction A2 of the light converging points P1 and FIG. 4(b) illustrates a state in which the light converging points P1 is scanned by the light scanner 21 viewed from the optical axis direction of the irradiation light L1. As illustrated in FIG. 4(a), in this example, when viewed from the optical axis direction of the irradiation light L1, the light converging points P1 are arranged in a direction A3 intersecting the scanning direction A2. Also, as illustrated in FIG. 4(b), there are a high-speed axis and a low-speed axis for scanning by the light scanner 21 and an operation in which the light converging point P1 is moved along the high-speed axis, shifted in a direction of the low-speed axis, and then moved again along the high-speed axis is iterated. In this example, the arrangement direction of the light converging points P1 viewed from the optical axis direction of the irradiation light L1 is along the low-speed axis (i.e., the axis intersecting the scanning direction A2). A direction A3 is orthogonal to the scanning direction A2 or inclined with respect to the scanning direction A2. Also, the light scanner 21 may scan the light converging point P1 so that the light converging point P1 also moves in the low-speed axis direction while moving along the high-speed axis. Also, not only line scanning but also tiling scanning may be used.

The plurality of light converging points P1 formed with the above-described positional relationship are implemented by the computer 53 for controlling the modulating pattern to be presented on the spatial light modulator 13 and the objective lens 32. The computer 53 controls the modulating pattern so that a plurality of light converging points P1 are formed in the observation object B. Then, the modulated irradiation light L1 is converged by the objective lens 32 and the plurality of light converging points P1 are formed in the observation object B.

Figure 5:
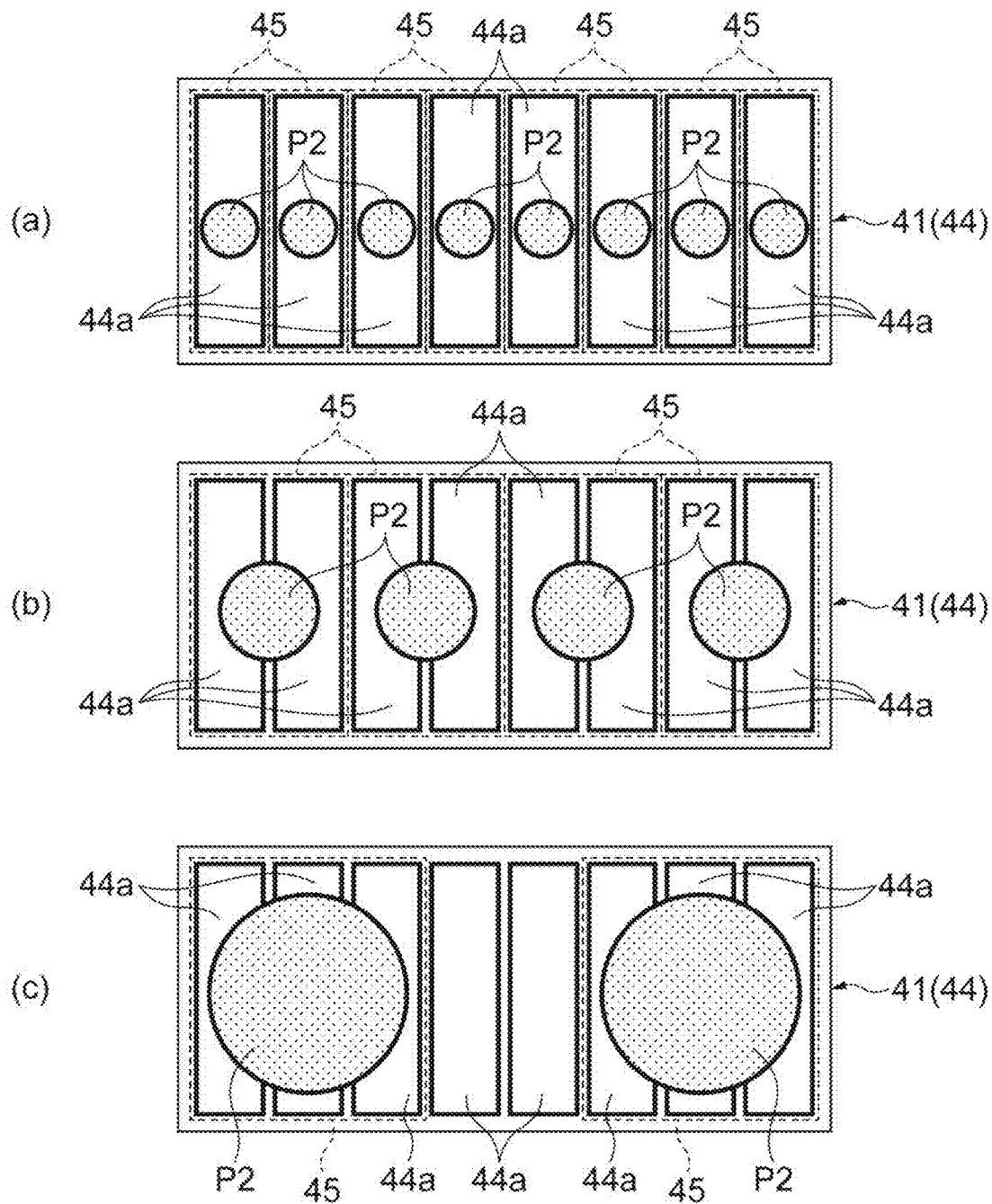
FIG. 5 is a front view illustrating a light detecting surface of a photodetector.

FIGS. 5(a) to 5(c) are front views illustrating a light detecting surface 44 of the photodetector 41 of the present embodiment. As illustrated in FIGS. 5(a) to 5(c), the light detecting surface 44 includes a plurality of light detecting units 44a. For example, when the photodetector 41 is a multi-anode PMT, the light detecting unit 44a corresponds to each anode of the multi-anode PMT. Also, for example, when the photodetector 41 is an area image sensor, the light detecting unit 44a corresponds to one pixel or pixel group. Also, for example, when the photodetector 41 is a photodiode array (line sensor), the light detecting unit 44a corresponds to each photodiode.

As illustrated in FIGS. 5(a) to 5(c), point images P2 of a plurality of observation lights generated from a plurality of light converging points P1 are formed on the light detecting surface 44. The photodetector 41 detects the plurality of observation lights by detecting light intensities of a plurality of point images P2. FIG. 5(a) illustrates a case in which the observation depth of the light converging point P1 is shallow, FIG. 5(c) illustrates a case in which the observation depth of the light converging point P1 is deep, and FIG. 5(b) illustrates a case in which the observation depth of the light converging point P1 is intermediate between these observation depths. Because a distance between the surface of the observation object B that gives the aberration and the light converging point P1 (i.e., a distance inside the observation object B) becomes longer when the observation depth of the light converging point P1 in the observation object B is deeper, the light diameter of the point image P2 of the observation light reaching the photodetector 41 increases. For example, in FIG. 5(a), because the observation depth of the light converging point P1 is shallow, the light diameter of the point image P2 is small. In contrast, in FIG. 5(c), because the observation depth of the light converging point P1 is deep, the light diameter of the point image P2 is large. A size of the light diameter of the point image P2 of the observation light reaching the photodetector 41 also differs according to a size of the distance between the focal point of the objective lens 32 and the light converging point P1.

The photodetector 41 has a plurality of detection areas 45 for detecting a plurality of point images P2. The plurality of detection areas 45 are independent of each other and each includes one or more light detecting units 44a. In the present embodiment, the sizes of the plurality of detection areas 45 and the center spacing between the detection areas 45 are set on the basis of positions of the plurality of light converging points P1 (i.e., observation depths) in the optical axis direction of the objective lens 32.

Specifically, in the example illustrated in FIG. 5(a), because the observation depth of the light converging point P1 is shallow, the sizes of the plurality of detection areas 45 are set to be small and the center spacing between the detection areas 45 is also set to be short. As an example, each detection area 45 is set to include one light detecting unit 44a and the center spacing between the detection areas 45 is set to be equal to the center spacing between the light detecting units 44a. In the example illustrated in FIG. 5(c), because the observation depth of the light converging point P1 is deep, the sizes of the plurality of detection areas 45 are set to be larger than those in FIG. 5(a) and the center spacing between the detection areas 45 is also set to be longer than that in FIG. 5(a). As an example, each detection area 45 may be set to include three light detecting units 44a, and the center spacing between the detection areas 45 may be set to be equal to the center spacings between every fifth light detecting unit 44a. In this case, detection signals from three light detecting units 44a are summed and a sum of the detection signals becomes the detection signal from the detection area 45. In the example illustrated in FIG. 5(b), because the observation depth of the light converging point P1 is intermediate between FIG. 5(a) and FIG. 5(c), the sizes of the plurality of detection areas 45 are set to be larger than those in FIG. 5(a) and smaller than those in FIG. 5(c), and the center spacing between the detection areas 45 is set to be longer than that in FIG. 5(a) and shorter than that in FIG. 5(c). As an example, each detection area 45 is set to include two light detecting units 44a, and the center spacing between the detection areas is set to be equal to the center spacings between every second light detecting unit 44a. In this case, the detection signals from the two light detecting units 44a are summed and a sum of the detection signals become a detection signal from the detection area 45. In many cases, the center spacing between the detection areas 45 becomes a value different from the center spacing W between the light converging points P1.

Figure 6:
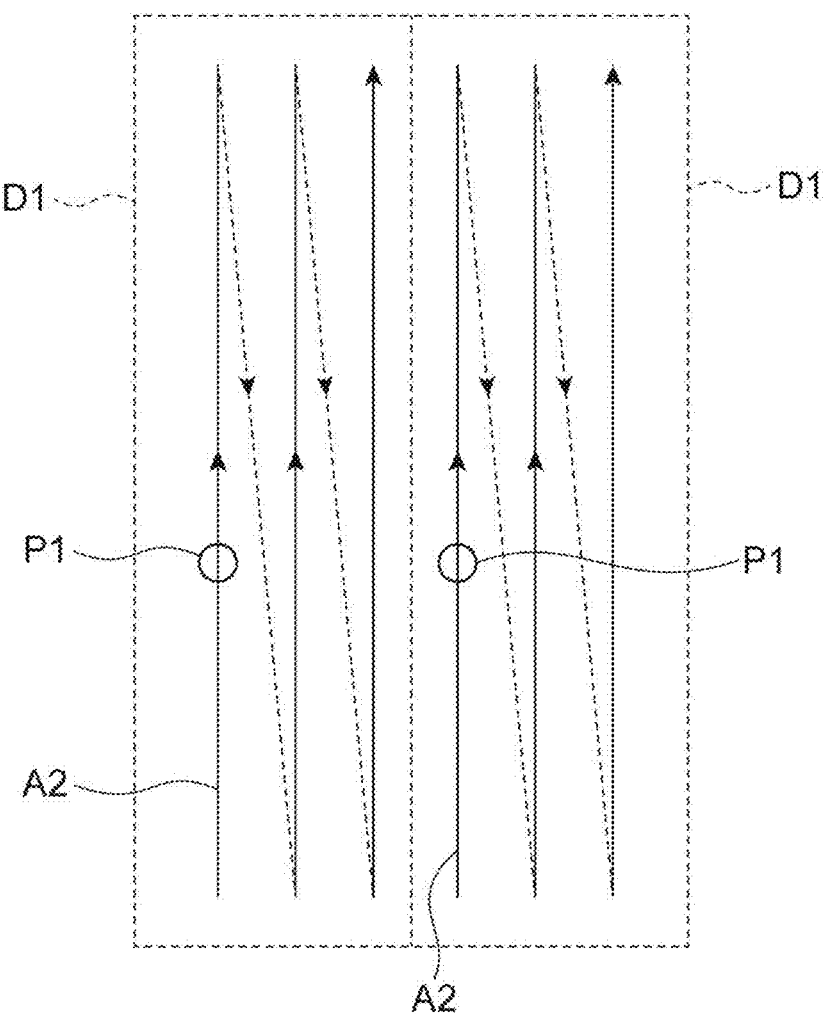
FIG. 6 is a diagram conceptually illustrating a plurality of image data included in a detection signal.

The computer 53 serving as an image creating unit creates an image of the observation object B on the basis of a detection signal Sd from the photodetector 41 and light irradiation position information in the light scanner 21. The detection signal Sd from the photodetector 41 includes a plurality of image data corresponding to the plurality of detection areas 45. FIG. 6 is a diagram conceptually illustrating a plurality of image data D1 included in the detection signal Sd. A plurality of elongated image data (strip images) D1 are generated from the plurality of observation light by scanning the plurality of light converging points P1 on the observation object B in the above-described manner. In other words, each piece of image data D1 is an image of the scanning area of each light converging point P1. In FIG. 6, two of the plurality of image data D1 are enlarged and illustrated. The computer 53 creates an image of the observation object B by mutually combining a plurality of image data D1. Thereby, an internal image of the observation object B at a desired observation depth can be created.

Also, each scanning area may be set so that the scanning areas of adjacent light converging points P1 partially overlap. In this case, for example, by combining a plurality of image data D1 while weighting overlapping portions, a boundary portion between pieces of image data D1 can be made inconspicuous.

Figure 7:
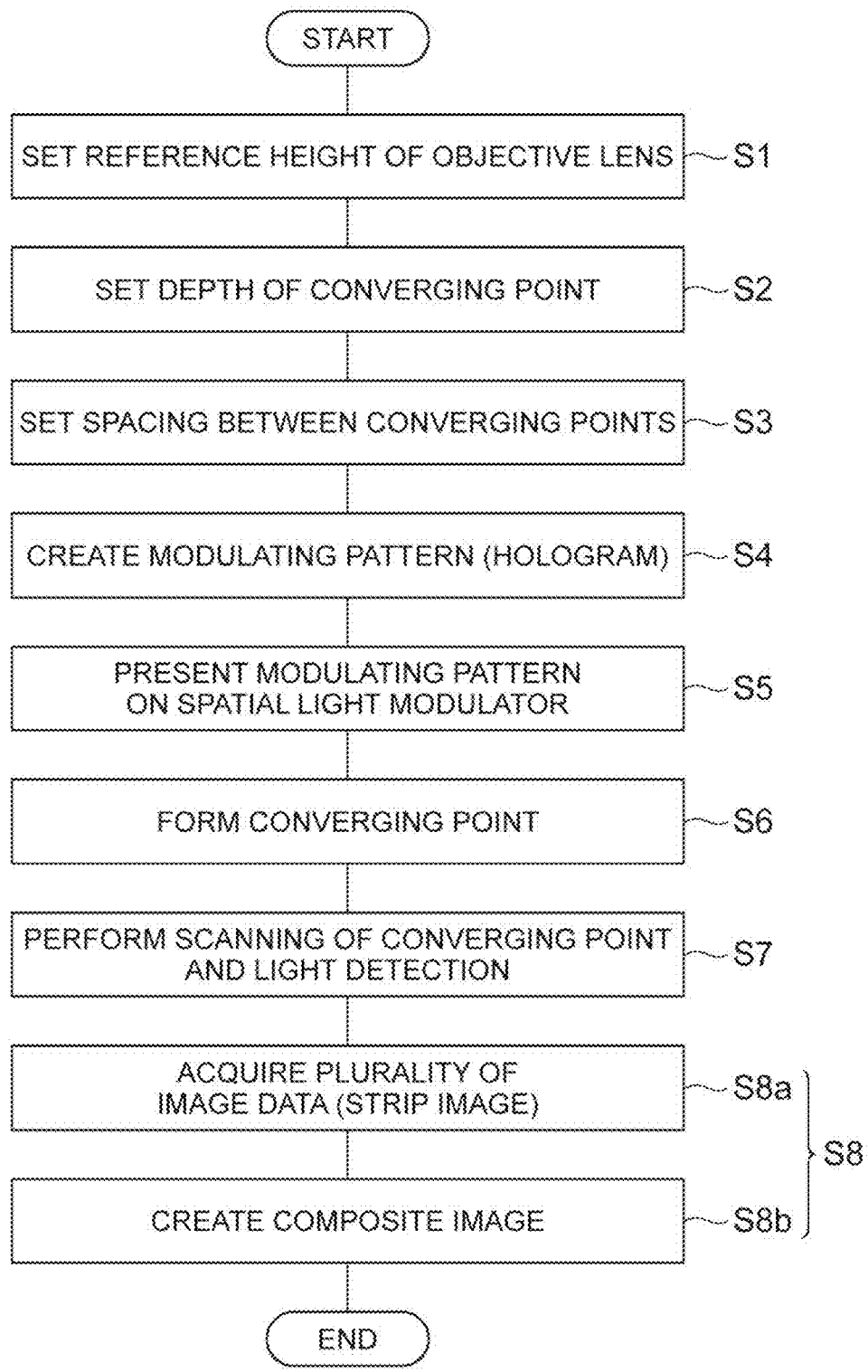
FIG. 7 is a flowchart of an image acquisition method.

Here, FIG. 7 is a flowchart illustrating the operation of the image acquisition device 1A described above. The image acquisition method according to the present embodiment will be described with reference to FIG. 7.

Figure 8:
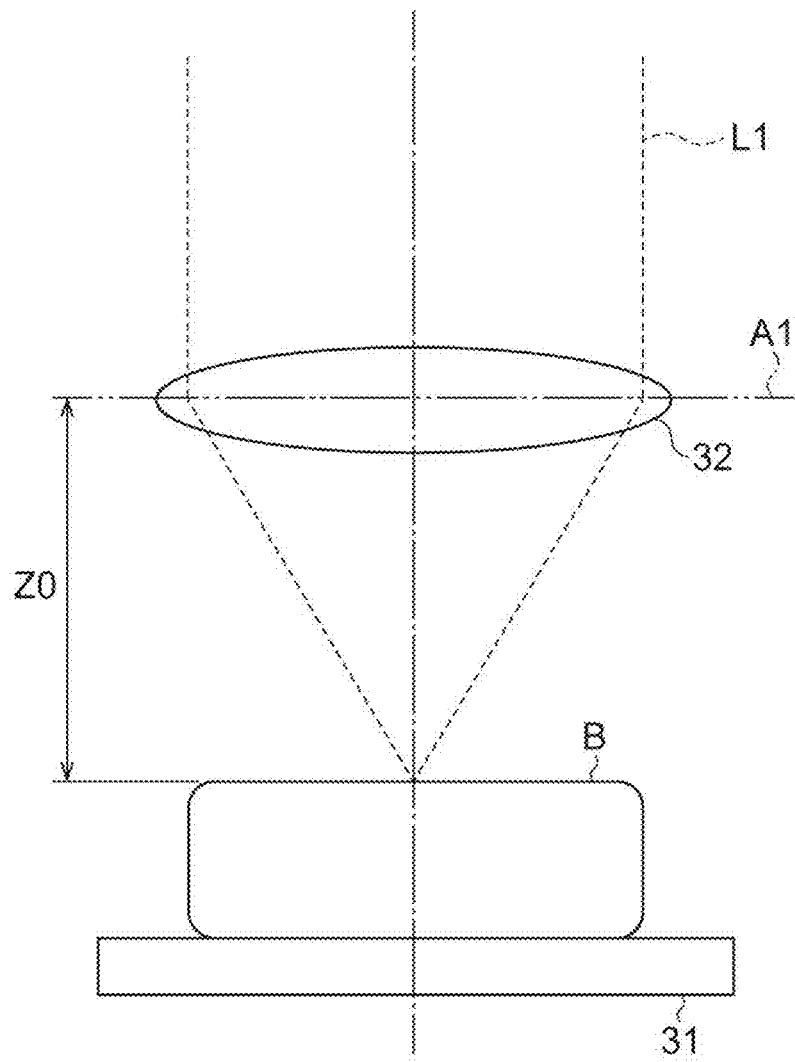
FIG. 8 is a diagram conceptually illustrating a state in which a reference height is set.

First, after the observation object B is placed on the stage 31, a reference height of the objective lens 32 is set (step S1). In step S1, a distance between the objective lens 32 and the observation object B is adjusted by the objective lens moving mechanism 33 or the stage 31 and the reference height is set. FIG. 8 is a diagram conceptually illustrating a state in which a reference height Z0 is set. For example, the height of the objective lens 32 may be adjusted so that the focal position of the objective lens 32 is aligned with the surface of the observation object B and a height thereof may be set as the reference height Z0. Also, by moving the stage 31 in the optical axis direction of the objective lens 32, the focal position of the objective lens 32 may be aligned with the surface of the observation object B. The computer 53 stores the reference height Z0.

Figure 9:
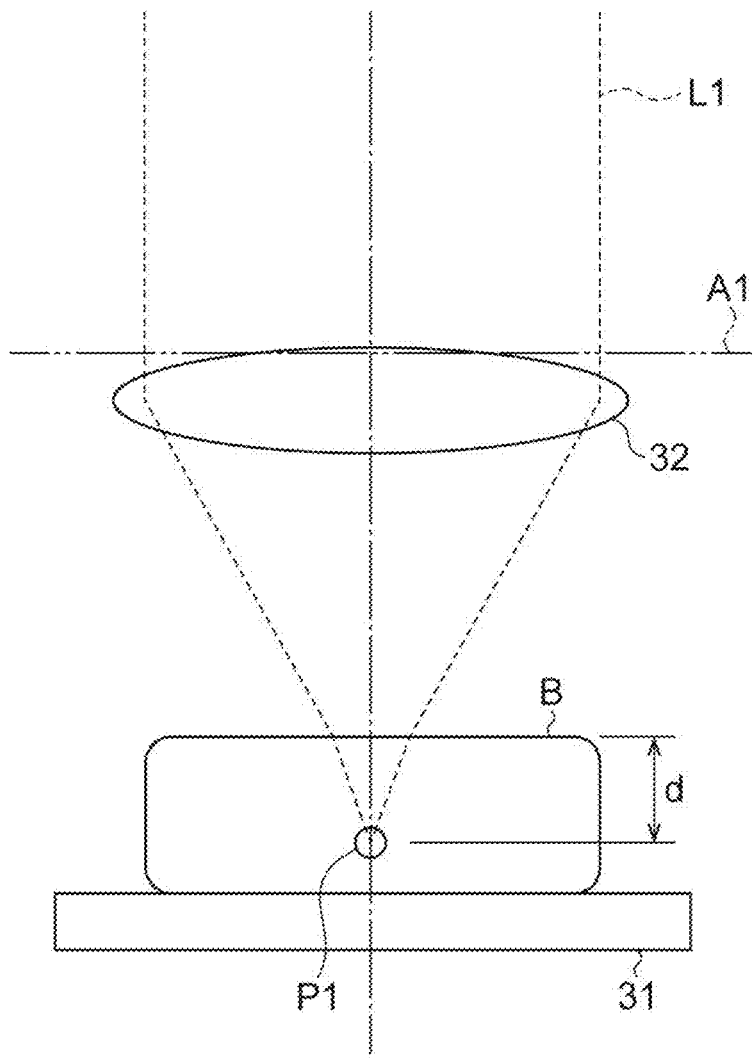
FIG. 9 is a diagram illustrating a state in which an observation depth of a light converging point is set.

Next, as illustrated in FIG. 9, the observation depth d of the light converging point P1, i.e., the depth inside the observation object B to be imaged, is set (step S2). In this step S2, for example, the observer may input an optical axis direction position of the objective lens 32 to the reference height Z0 or input a depth from the surface of the observation object B, via the input device 51. The depth inside the observation object B may be an actual distance or an optical distance. Also, in consideration of a refractive index of the medium (such as air, water, oil, glycerin, silicone, or the like) between the objective lens 32 and the observation object B and/or the refractive index of the observation object B, an amount by which the objective lens 32 (or the stage 31) is actually moved may be calculated. For example, in this case, when an observation depth d of the light converging point P1 is an optical distance, a refractive index of the medium is set as $n_a$, and a refractive index of the observation object B is set as $n_b$, a movement amount of the objective lens 32 (or the stage 31) is calculated as $n_b \cdot d/n_a$.

Subsequently, the center spacing W between the light converging points P1 is set (step S3). In step S3, as illustrated in FIGS. 2 and 3, it is preferable to further increase the center spacing W when the depth d of the light converging point P1 becomes deeper. Also, for example, the center spacing W may be set on the basis of parameters such as the numerical aperture (NA) of the objective lens 32, the refractive index of the medium between the objective lens 32 and the observation object B, the refractive index of the observation object B, the wavelength of the irradiation light L1, the surface shape and/or internal structure of the observation object B, and the amounts of aberration on the surface and/or the inside of the observation object B. These parameters may be obtained through actual measurement or may be estimated and obtained through simulation or the like. Also, center spacings W corresponding to depths d may be calculated in advance and stored as a table in a storage area of the computer 53, and an appropriate center spacing W may be selected from the storage area.

Subsequently, a modulating pattern (hologram) is created (step S4). In this step S4, a computer generated hologram (CGH) to be presented on the spatial light modulator 13 is created on the basis of spacing W between the light converging points P1 and depths d thereof set in the above-described steps S2 and S3. This step S4 is performed by, for example, the computer 53. Alternatively, CGHs corresponding to the depths d and the spacing W may be calculated in advance and stored as a table in a storage means inside the computer 53, and an appropriate CGH may be selected from among the CGHs.

Subsequently, the CGH created in step S4, i.e., a modulating pattern in which a plurality of light converging points P1 are formed in the observation object B, is presented on the spatial light modulator 13 (pattern presenting step S5). Then, the irradiation light L0 output from the light source 11 is modulated in the spatial light modulator 13, and the modulated irradiation light L1 is converged by the objective lens 32, so that the plurality of light converging points P1 are formed at the depth d of the observation object B (light converging point forming step S6). In steps S5 and S6, the distance between the objective lens 32 and the observation object B is adjusted so that the light converging point P1 is formed at the depth d inside the observation object B. In this state, the CGH is presented on the spatial light modulator 13, so that the irradiation light L0 output from the light source 11 is modulated, the modulated irradiation light L1 is concentrated by the objective lens 32, and the plurality of light converging points P1 at the position of the depth d inside the observation object B are formed with the spacing W. Also, after the distance between the objective lens 32 and the observation object B is adjusted, the CGH may be presented on the spatial light modulator 13 and the modulated irradiation light L1 may be converged by the objective lens 32.

Subsequently, scanning and light detection of the plurality of light converging points P1 are performed (light detecting step S7). In this light detecting step S7, while the positions of the plurality of light converging points P1 inside the observation object B are scanned in the scanning direction intersecting the optical axis of the irradiation light L1, the observation light L2 generated from the plurality of light converging points P1 is detected. At this time, because a plurality of observation lights L2 are de-scanned by the light scanner 21, it is possible to fixedly detect the position of the point image P2 of the observation light L2 in the photodetector 41 while moving the light converging point P1. From the photodetector 41, a detection signal Sd including a plurality of image data corresponding to a plurality of point images P2 is output to the computer 53.

Subsequently, an image of the observation object B is created (image creating step S8). In this image creating step S8, an image of the observation object B is created by the computer 53 using the detection signal Sd (light intensity information) obtained in the light detecting step S7 and the optical scanning position information from the light scanner 21. Specifically, as illustrated in FIG. 6, a plurality of image data D1 are acquired from the detection signal Sd and the light scanning position information (step S8a) and the image of the observation object B is created by mutually combining the plurality of image data D1 (step S8b).

Effects of the image acquisition device 1A and the image acquisition method of the present embodiment described above will be described. In the image acquisition device 1A and the image acquisition method of the present embodiment, the modulating pattern is presented on the spatial light modulator 13, so that it is possible to simultaneously and easily form the plurality of light converging points P1. Then, the plurality of light converging points P1 are scanned (scanned), and the point image P2 of the plurality of observation lights generated at these light converging points P1 is detected by the photodetector 41. As described above, according to each of the image acquisition device 1A and the image acquisition method of the present embodiment, it is possible to simultaneously irradiate the observation object B with a plurality of irradiation lights L1 and simultaneously detect a plurality of observation lights L2. Accordingly, it is possible to shorten the observation time and easily acquire states of a plurality of portions at the same time.

When the observation object B is, for example, a biological sample, the observation time can be shortened, the load on a living body can be reduced, and observation in a better state becomes possible. For example, it is difficult to observe the living body in a living state when a time period of 100 minutes is required for three-dimensional imaging, but observation is considered to be possible in the living state if the time period is 10 minutes.

Figure 10:
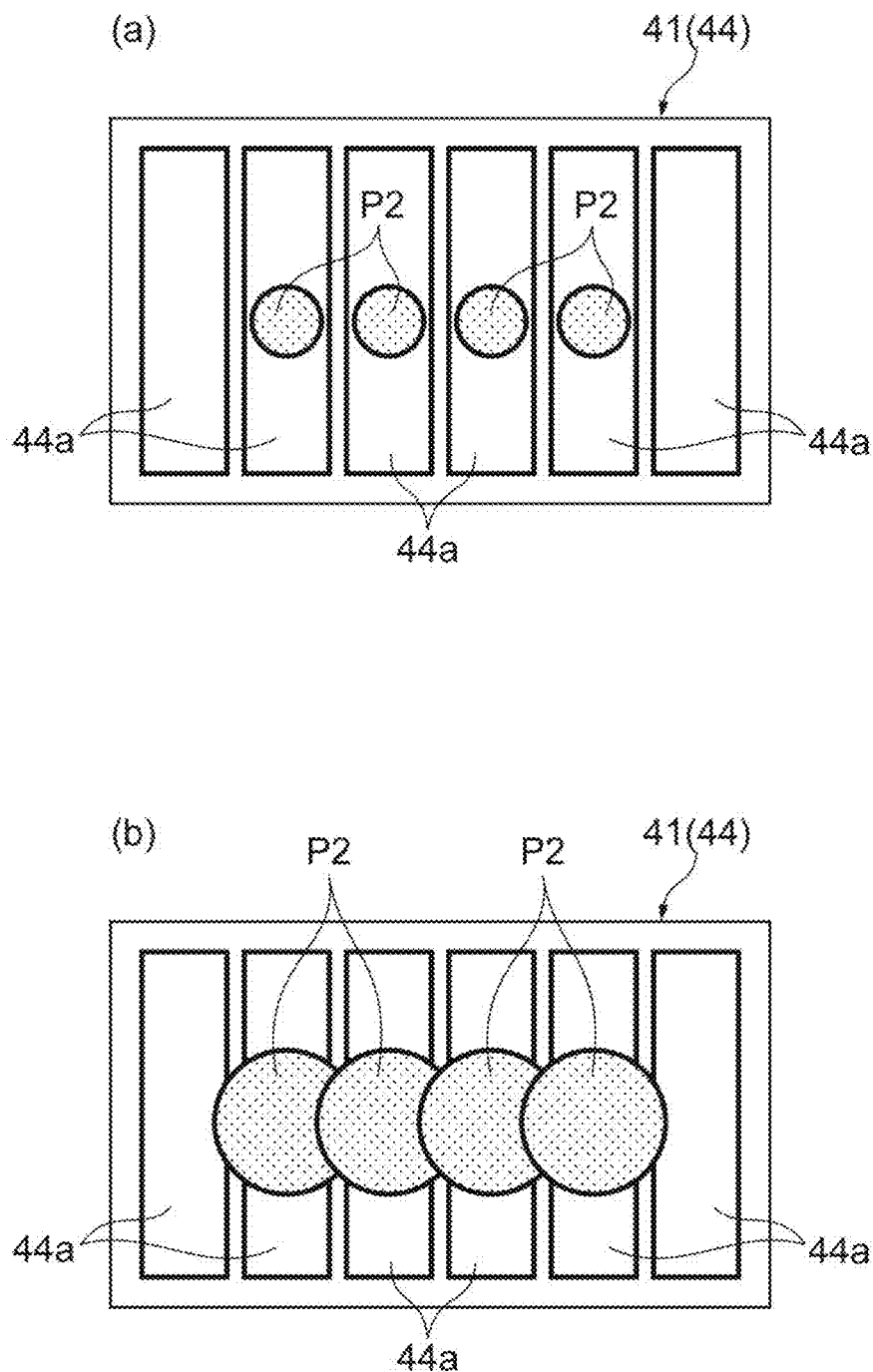
FIG. 10 is a diagram illustrating a state in which adjacent point images overlap in the photodetector and crosstalk occurs.

Also, when a plurality of observation lights L2 generated from a plurality of positions are simultaneously detected, adjacent point images P2 overlap each other in the photodetector 41 according to the observation depth d and crosstalk may occur. FIG. 10 is a diagram illustrating such a phenomenon. As illustrated in FIG. 10(a), a case in which point images P2 of a plurality of observation lights are incident on a plurality of detection areas 45 at a certain observation depth d is considered. As described above, the light diameter of the observation light generated at a deep position in the observation object B due to the aberration at the surface of the observation object B is larger than the light diameter of the observation light generated at a shallow position (see FIG. 5). Here, the aberration on the surface of the observation object B includes, for example, spherical aberration caused by a refractive index difference between the immersion liquid or air used for observation and the observation object B, astigmatism occurring when a refractive index boundary is not perpendicular to the optical axis, coma aberration, defocus aberration, and the like. In particular, the spherical aberration tends to increase as the observation depth d increases. Also, the light diameter of the observation light generated at a deep position in the observation object B due to aberration (spherical aberration, astigmatism, coma aberration, defocus aberration, or the like) inside the observation object B is greater than the tight diameter of the observation light generated at a shallow position (see FIG. 5). Accordingly, as illustrated in FIG. 10(b), the point images P2 of adjacent observation lights in the photodetector 41 overlap each other according to the observation depth d and crosstalk may occur. When crosstalk occurs, it becomes difficult to accurately detect each of the plurality of observation lights L2.

On the other hand, in the image acquisition device 1A and the image acquisition method of the present embodiment, as illustrated in FIGS. 2 and 3, the center spacing W between adjacent light converging points P1 is set on the basis of positions of a plurality of light converging points P1 (that is, observation depths d) in the optical axis direction of the objective lens 32. Thereby, for example, when the light diameter of the point image P2 of the observation light in the photodetector 41 is increased, the center spacing W between the light converging points P1 can be widened, so that it is possible to prevent the point images P2 from overlapping each other and crosstalk can be reduced. Also, in the image acquisition device 1A and the image acquisition method according to the present embodiment, the center spacing W between adjacent light converging points P1 is further set on the basis of the amounts of aberration on the surface and/or the inside of the observation object B. Thereby, because the center spacing W between adjacent light converging points P1 is set in consideration of the amounts of aberration on the surface and/or the inside of the observation object B, it is possible to further suppress the overlapping of the plurality of point images P2 and reduce crosstalk. Accordingly, it is possible to accurately detect point images P2 of a plurality of observation lights and provide an image of a clear observation object.

Also, in the present embodiment, the plurality of light converging points P1 refer to light converging points having the same amount of light. For example, a light converging point where the amount of light is significantly smaller than the other light converging points and does not contribute to image creation is not included in the light converging points used here. In other words, the light converging point P1 in the present embodiment refers to a light converging point for generating the observation light L2 useful for image creation.

Also, by forming a plurality of light converging points P1 using the modulating pattern to be presented in the spatial light modulator 13, it is possible to easily converge light on a desired position in a direction perpendicular or parallel to the optical axis direction of the irradiation light L1 and it is possible to easily change the number of light converging points, a position, an intensity, and the like.

Also, as in the present embodiment, the computer 53 may increase the center spacing W as the plurality of light converging points P1 are distanced further from the surface of the observation object B. Thereby, the crosstalk of the observation light caused by the aberration of the surface of the observation object B can be suitably reduced.

Also, as in the present embodiment, the photodetector 41 has a plurality of detection areas 45 for detecting the point images P2 of the plurality of observation lights, and the sizes of the plurality of detection areas 45 and a center spacing between the detection areas 45 may be set on the basis of the positions of the plurality of light converging points P1 in the direction of the optical axis of the objective lens 32. Thereby, because the pitch between and sizes of the plurality of detection areas 45 are set according to the center spacing between the point images P2 in the photodetector 41 and/or the light diameter, it is possible to suitably detect the plurality of observation lights L2.

Also, as in the present embodiment, the photodetector 41 outputs a plurality of image data D1 corresponding to the plurality of detection areas 45 as the detection signal Sd, and the computer 53 may create an image of the observation object B by combining a plurality of image data D1 in the image generation step S8. Thereby, because it is possible to divide an area to be observed in the observation object B into a plurality of areas and create images of the areas in parallel, an observation time can be effectively shortened.

Also, as in the present embodiment, the photodetector 41 may include a multi-anode photomultiplier tube having a plurality of anodes or may include an area image sensor having a plurality of pixels. According to any one thereof, it is possible to accurately detect the light intensity of the observation light L2 in each of the plurality of point images P2.

Also, as in the present embodiment, a plurality of light converging points P1 may be arranged in a direction intersecting the scanning direction A2 when viewed from the optical axis direction of the objective lens 32. Thereby, because it is possible to divide an area to be observed in the observation object B into a plurality of areas and create images of the areas in parallel, an observation time can be effectively shortened.

Also, in this embodiment, the modulating pattern to be presented on the spatial light modulator 13 may include an aberration correction pattern for the irradiation light L1. Thereby, it is possible to increase the resolution of measurement by reducing the size of the light converging points P1.

As a result, a wide observation area can be observed with a small spacing. According to this embodiment, because a plurality of light converging points P1 are simultaneously irradiated and point images P2 of a plurality of observation lights are simultaneously detected, the observation time can be effectively shortened and, for example, it is possible to prevent an increase in the observation time or to perform observation in a significantly short time even under conditions in which more observation time is required in observation with a single light converging point P1.

First Modified Example

Figure 11:
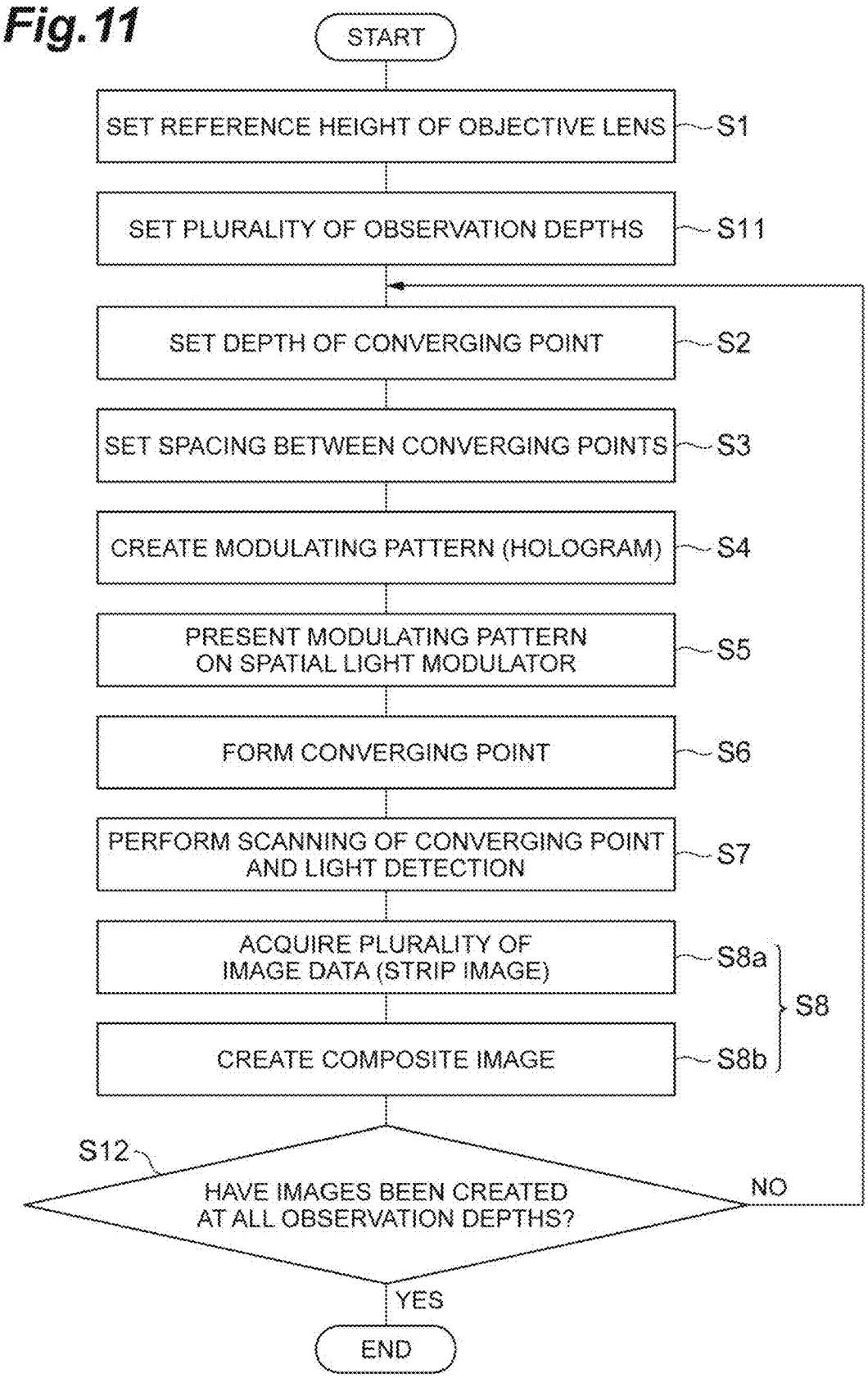
FIG. 11 is a flowchart of an image acquisition method according to a first modified example.

FIG. 11 is a flowchart of an image acquisition method according to a first modified example of the above-described embodiment. An image at a certain observation depth d of the observation object B is acquired in the above-described embodiment, but an image is obtained while the observation depth d from the surface of the observation object B is sequentially changed in the present modified example. Steps S1 to S8 illustrated in FIG. 11 are the same as those in the above-described embodiment and the description thereof will be omitted.

In this modified example, after the reference height Z0 of the objective lens 32 is set (step S1), the computer 53 sets a plurality of observation depths d (step S11). The plurality of observation depths d may be set by an observer via the input device 51 or may be automatically set by the computer 53 on the basis of an image acquisition range input by the observer.

Subsequently, as in the above-described embodiment, steps S2 to S8 are performed. Thereafter, if no image has been prepared for all the observation depths d (step S12: NO), the process returns to step S2 again and the computer 53 resets the depth d of the light converging point P1 to change the depth d. At this time, in step S3, the computer 53 changes the center spacing W according to the change in the observation depth d. Specifically, the computer 53 further widens the center spacing W when the light converging point P1 is further away from the surface of the observation object B. If an image has been created for all observation depths d (step S12: YES), the process is terminated.

As in the present modified example, the computer 53 may change the center spacing W in accordance with a change in positions of the plurality of light converging points P1 (i.e., observation depths d) in the optical axis direction of the objective lens 32. Thereby, observation at a plurality of observation depths d can be continuously performed while crosstalk is suppressed. In this case, the computer 53 may increase the center spacing W as the plurality of light converging points P1 are distanced further from the surface of the observation object B. Thereby, the crosstalk of the observation light caused by the aberration of the surface of the observation object B can be suitably reduced.

Second Modified Example

In the above-described embodiment, the light converging point P1 can be scanned by the light scanner 21. However, the light converging point P1 may be scanned by moving the stage 31 in a plane direction intersecting the optical axis direction. In other words, the scanning unit of the above-described embodiment may include the stage 31 in place of the light scanner 21 or together with the light scanner 21. Also in such a configuration, it is possible to suitably scan the light converging point P1.

Third Modified Example

In the above-described embodiment, the light converging point P1 is scanned by the light scanner 21. However, a pattern (light scanning hologram) for scanning the light converging point P1 may be included (superimposed) in the modulating pattern to be presented on the spatial light modulator 13. In this case, because the scanning unit in the above-described embodiment is unnecessary, it is possible to reduce the number of components of the image acquisition device 1A and contribute to size reduction.

Example

Here, an example of the above-described embodiment will be described. In the present example, a resin containing a plurality of fluorescent beads each having a diameter of 3 μm was prepared as the observation object B. This resin was observed using an objective lens (having 40x water immersion and NA of 1.15). An image was acquired by forming a plurality of light converging points P1 at a position of the depth d and scanning the light converging points P1. At this time, the plurality of light converging points P1 was arranged in the direction A3 intersecting the scanning direction A2. Also, the observation depth d was 5 μm and 250 μm. Also, in the following drawings, an arrow A4 of the drawing indicates a scanning start position of the plurality of light converging points P1 in the direction A3.

Figure 12:
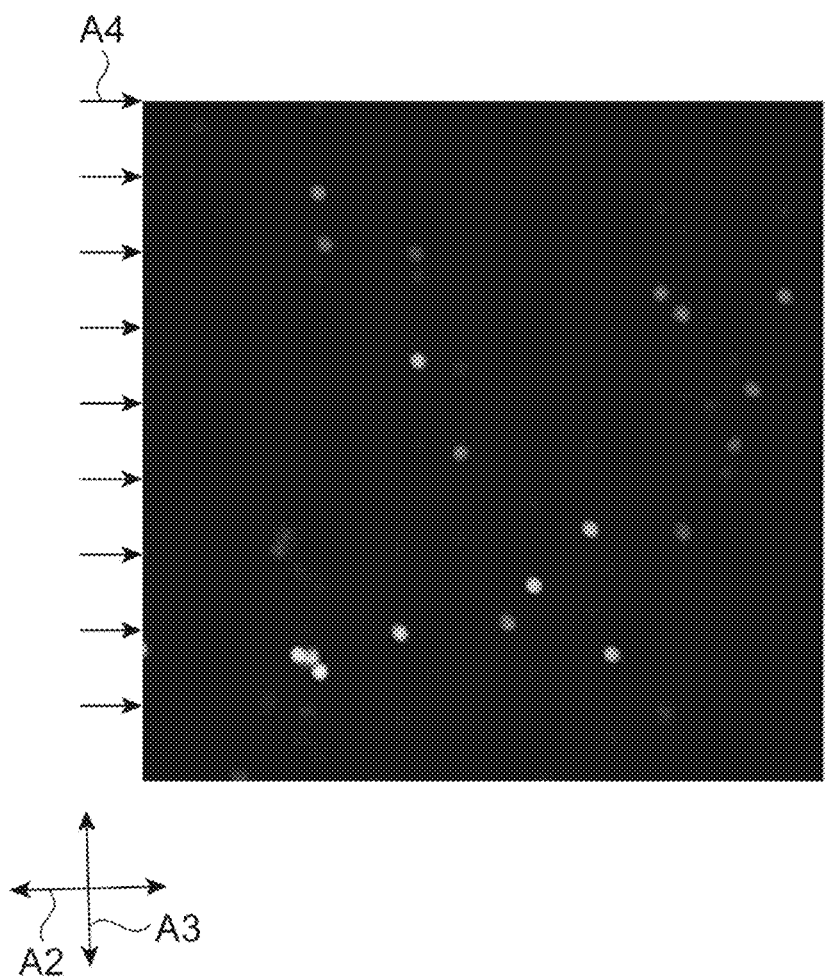
FIG. 12 illustrates an image acquired in an example.

FIG. 12 illustrates an obtained image when the observation depth d was 5.68 μm as an optical distance and a center spacing W between the light converging points P1 was 13.7 μm. At this time, clear fluorescence images could be acquired.

Figure 13:
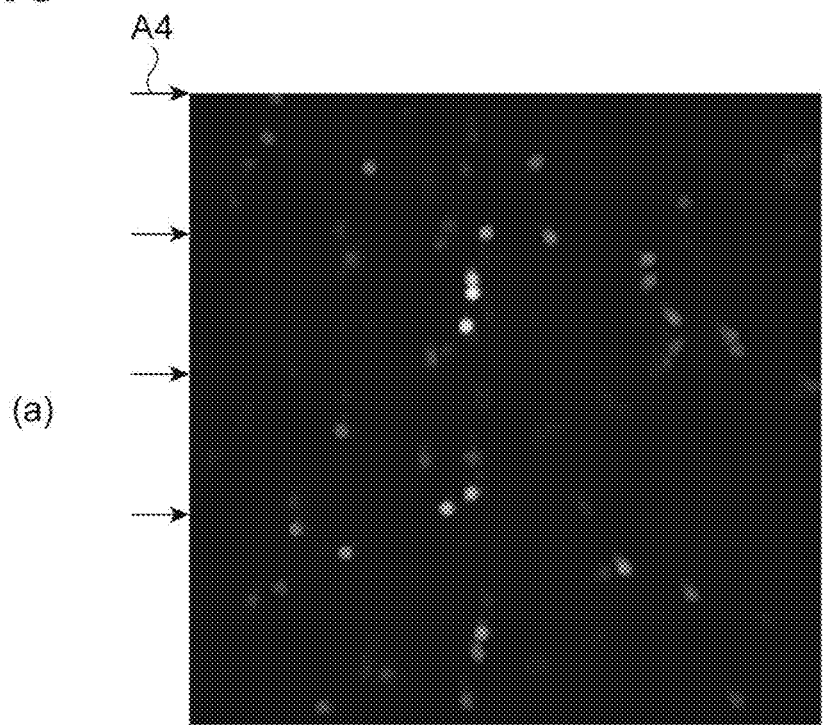
FIG. 13 illustrates an image acquired in an example.
Figure 13:
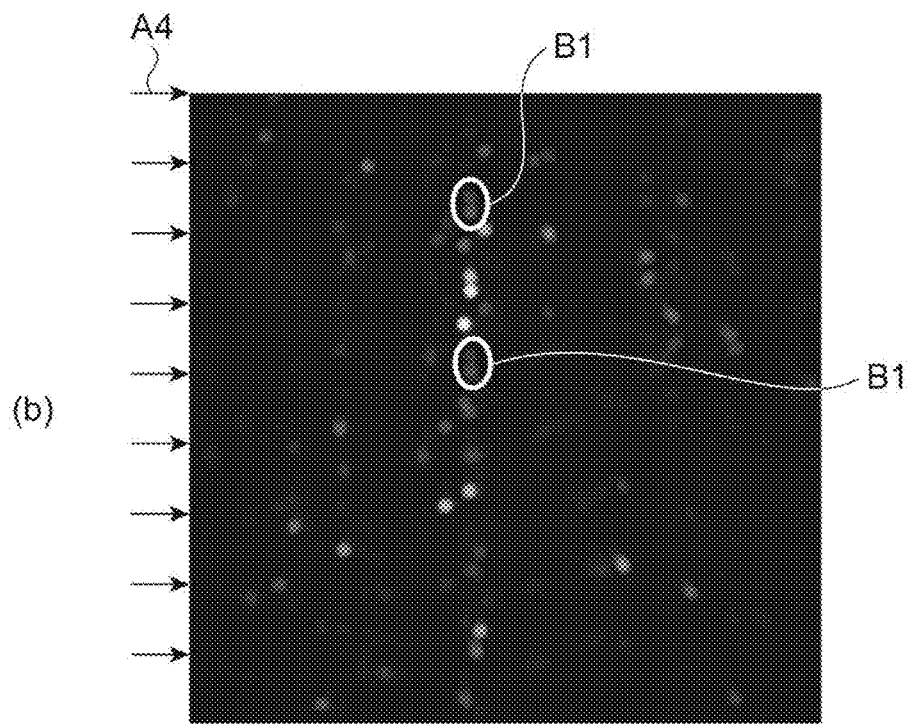

Further, FIG. 13 illustrates an image obtained by setting the observation depth d to 292 μm as an optical distance. FIG. 13(a) is an image obtained with the center spacing W of the plurality of light converging points P1 was set to 27.4 μm, and FIG. 13(b) is an obtained image when the center spacing W between the light converging points P1 was 13.7 μm. As illustrated in FIG. 13(b), when the observation depth d was changed to 292 μm and the center spacing W of 13.7 μm was not changed, there was one fluorescent bead originally, but a plurality of fluorescent beads appeared due to the influence of crosstalk of the observation light (see a range B1 in FIG. 13(b)). On the other hand, as illustrated in FIG. 13(a), when the center spacing W was changed to 27.4 μm on the basis of the observation depth d (292 μm), clear fluorescence images in which the influence of crosstalk was suppressed could be acquired.

INDUSTRIAL APPLICABILITY

It is possible to simultaneously radiate a plurality of lights for which light converging positions are different in a depth direction of an observation object.

REFERENCE SIGNS LIST

1A Image acquisition device
10 Irradiation light generating unit
11 Light source
12 Beam expander
13 Spatial light modulator
14 Dichroic mirror
20 Scanning unit
21 Light scanner
22 Mirror
30 Irradiation optical unit
31 Stage
32 Objective lens
33 Objective lens moving mechanism
34 Reflection mirror
40 Observation unit
41 Photodetector
42 Filter
43 Condenser lens
44 Light detecting surface
44a Light detecting unit
45 Detection area
50 Control unit
51 Input device
52 Display device
53 Computer
61, 62 Telecentric optical system
B Observation object
D1 Image data
L1 Irradiation light
L2 Observation light
P1 Light converging point
P2 Point image
Sd Detection signal

The invention claimed is:

1. An image acquisition device comprising:
a spatial light modulator configured to modulate irradiation light output from a light source;
a controller configured to control a modulating pattern to be presented on the spatial light modulator so that a plurality of light converging points are formed in an observation object;
a lens configured to converge the modulated irradiation light so that the plurality of light converging points are formed in the observation object;
a scanner configured to scan positions of the plurality of light converging points in the observation object in a scanning direction intersecting an optical axis of the lens;
a photodetector configured to detect a plurality of observation lights generated from the plurality of light converging points;
a telecentric optical system provided on an optical axis of the irradiation light and the observation light, the telecentric optical system configured to transfer a wavefront of the irradiation light generated in the spatial light modulator to a rear focal point of the lens; and
a dichroic mirror arranged at a position at which the irradiation light modulated by the spatial light modulator and the observation light de-scanned by the scanner are received,
wherein the controller is configured to set a center spacing between adjacent light converging points on the basis of the positions of the plurality of light converging points in a direction of the optical axis of the lens,
wherein the telecentric optical system is a double-sided telecentric optical system and is adjusted to form an image on a modulation surface of the spatial light modulator and a scanning surface of the scanner, and
wherein the dichroic mirror transmits at least a part of the irradiation light, and reflects at least a part of the observation light.

2. The image acquisition device according to claim 1, wherein the controller is configured to change the center spacing according to a change in the positions of the plurality of light converging points in the direction of the optical axis of the lens.

3. The image acquisition device according to claim 2, wherein the controller is configured to increase the center spacing as the positions of the plurality of light converging points in the direction of the optical axis of the lens are distanced further from a surface of the observation object.

4. The image acquisition device according to claim 1, wherein the scanner includes a light scanner configured to receive the modulated irradiation light.

5. The image acquisition device according to claim 1, wherein the scanner includes a stage configured to move the observation object in the scanning direction while holding the observation object.

6. The image acquisition device according to claim 1, wherein the photodetector has a plurality of detection areas for detecting the plurality of observation lights, and
wherein sizes of the plurality of detection areas and a center spacing between the detection areas are set on the basis of the positions of the plurality of light converging points in the direction of the optical axis of the lens.

7. The image acquisition device according to claim 6, further comprising a computer configured to create an image of the observation object using a detection signal from the photodetector,
wherein the photodetector is configured to output a plurality of image data corresponding to the plurality of detection areas as the detection signal, and
wherein the computer is configured to combine the plurality of image data to create the image of the observation object.

8. The image acquisition device according to claim 6, wherein the photodetector includes a multi-anode photomultiplier tube having a plurality of anodes.

9. The image acquisition device according to claim 6, wherein the photodetector includes an area image sensor having a plurality of pixels.

10. The image acquisition device according to claim 6, wherein the photodetector includes an avalanche photodiode array having a plurality of avalanche photodiodes.

11. The image acquisition device according to claim 1, wherein the plurality of light converging points are arranged in a direction intersecting the scanning direction when viewed from the direction of the optical axis of the lens.

12. The image acquisition device according to claim 1, wherein the controller is configured to set the center spacing between adjacent light converging points on the basis of amounts of aberration on a surface and/or an inside of the observation object.

13. An image acquisition device comprising:
a spatial light modulator configured to modulate irradiation light output from a light source;
a controller configured to control a modulating pattern to be presented on the spatial light modulator so that a plurality of light converging points are formed in an observation object;
a lens configured to converge the modulated irradiation light so that the plurality of light converging points are formed in the observation object;
a photodetector configured to detect a plurality of observation lights generated from the plurality of light converging points;
a telecentric optical system provided on an optical axis of the irradiation light and an optical axis of the observation light, the telecentric optical system configured to transfer a wavefront of the irradiation light generated in the spatial light modulator to a rear focal point of the lens; and
a dichroic mirror arranged at a position at which the irradiation light modulated by the spatial light modulator is received,
wherein the modulating pattern includes a pattern for scanning the plurality of light converging points in a scanning direction intersecting the optical axis of the irradiation light,
wherein the controller is configured to set a center spacing between adjacent light converging points on the basis of positions of the plurality of light converging points in a direction of the optical axis of the irradiation light,
wherein the telecentric optical system is a double-sided telecentric optical system and is adjusted to form an image on a modulation surface of the spatial light modulator, and
wherein the dichroic mirror transmits at least a part of the irradiation light, and reflects at least a part of the observation light.

14. An image acquisition method comprising:
by a spatial light modulator, modulating irradiation light output from a light source based on a modulating pattern for forming a plurality of light converging points in an observation object;
converging the modulated irradiation light by a lens so that the plurality of light converging points are formed in the observation object;
scanning positions of the plurality of light converging points in the observation object in a scanning direction intersecting an optical axis of the irradiation light;
detecting a plurality of observation lights generated from the plurality of light converging points while scanning the positions and generating a detection signal; and
creating an image of the observation object based on the detection signal,
wherein a center spacing between adjacent light converging points is set on the basis of the positions of the plurality of light converging points in a direction of the optical axis by the modulating,
wherein a wavefront of the irradiation light is transferred by a double-sides telecentric optical system to a rear focal point of the lens,
wherein at least a part of the irradiation light is transmitted by a dichroic mirror, and at least a part of the observation light is reflected by the dichroic mirror.

15. The image acquisition method according to claim 14, wherein the center spacing is changed according to a change in the positions of the plurality of light converging points in the direction of the optical axis by the modulating.

16. The image acquisition method according to claim 15, wherein the center spacing is increased as the positions of the plurality of light converging points in the direction of the optical axis are distanced further from a surface of the observation object by the modulating.

17. The image acquisition method according to claim 14, wherein the scanning is performed using a light scanner receiving the modulated irradiation light in the detecting.

18. The image acquisition method according to claim 14, wherein the scanning is performed using a stage moving the observation object in the scanning direction while holding the observation object in the detecting.

19. The image acquisition method according to claim 14, wherein the scanning is performed using the spatial light modulator by modulating the irradiation light based on a pattern for scanning the plurality of light converging points superimposed on the modulating pattern in the detecting.

20. The image acquisition method according to claim 14, wherein a photodetector having a plurality of detection areas for detecting the plurality of observation lights is used in the detecting, and
wherein sizes of the plurality of detection areas and a center spacing between the detection areas are set on the basis of the positions of the plurality of light converging points in the direction of the optical axis.

21. The image acquisition method according to claim 20, wherein the photodetector is configured to output a plurality of image data corresponding to the plurality of detection areas as the detection signal, and
wherein the plurality of image data are combined to create an image of the observation object in the creating.

22. The image acquisition method according to claim 14, wherein the plurality of the observation lights are detected using a multi-anode photomultiplier tube having a plurality of anodes in the detecting.

23. The image acquisition method according to claim 14, wherein the plurality of the observation lights are detected using an area image sensor having a plurality of pixels in the detecting.

24. The image acquisition method according to claim 14, wherein the plurality of the observation lights are detected using an avalanche photodiode array having a plurality of avalanche photodiodes in the detecting.

25. The image acquisition method according to claim 14, wherein the plurality of light converging points are arranged in a direction intersecting the scanning direction when viewed from the direction of the optical axis.

26. The image acquisition method according to claim 14, wherein the center spacing between adjacent light converging points is further set on the basis of amounts of aberration on a surface and/or an inside of the observation object.

* * * * *